(12) United States Patent
Ekman et al.

(10) Patent No.: US 9,572,937 B2
(45) Date of Patent: Feb. 21, 2017

(54) AUTOINJECTOR HAVING PISTON ROD WITH NON-CIRCULAR AXIAL BORE SLIDABLY ARRANGED ON HOUSING SHAFT TO PREVENT RELATIVE ROTATION

(75) Inventors: Matthew Ekman, Macclesfield (GB); Timothy Donald Barrow-Williams, St. Albans (GB); Yannick Hourmand, Haslingfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1168 days.

(21) Appl. No.: 13/579,339

(22) PCT Filed: Feb. 16, 2011

(86) PCT No.: PCT/EP2011/052298
§ 371 (c)(1),
(2), (4) Date: Jan. 22, 2013

(87) PCT Pub. No.: WO2011/101376
PCT Pub. Date: Aug. 25, 2011

(65) Prior Publication Data
US 2013/0112521 A1 May 9, 2013

(30) Foreign Application Priority Data
Feb. 18, 2010 (EP) .................................. 10153989

(51) Int. Cl.
*A61M 5/20* (2006.01)
*A61M 5/32* (2006.01)
*A61M 5/46* (2006.01)

(52) U.S. Cl.
CPC ............... *A61M 5/20* (2013.01); *A61M 5/326* (2013.01); *A61M 5/46* (2013.01);
(Continued)

(58) Field of Classification Search
CPC ........ A61M 5/20; A61M 5/325; A61M 5/315; A61M 5/326; A61M 5/46; F16D 11/14
See application file for complete search history.

(56) References Cited

U.S. PATENT DOCUMENTS 4,973,318 A * 11/1990 Holm ...................... A61M 5/24
604/208
5,112,317 A * 5/1992 Michel .................... A61M 5/24
222/386

(Continued)

FOREIGN PATENT DOCUMENTS

| WO | 2006/045526 A1 | 5/2006 |
| WO | 2006/126902 A1 | 11/2006 |
| WO | 2009/037141 A1 | 3/2009 |

OTHER PUBLICATIONS

International Preliminary Report on Patentability for Int. App. No. PCT/EP2011/052298, mailed Aug. 30, 2012.

(Continued)

*Primary Examiner* — Bhisma Mehta
*Assistant Examiner* — Matthew A Engel
(74) *Attorney, Agent, or Firm* — Fish & Richardson P.C.

(57) ABSTRACT

The invention relates to a clutch mechanism for the transmission of a rotary movement from a gear arrangement comprising a first gear member and a second gear member. The first gear member is rotatable about a longitudinal axis but axially fixed wherein the first gear member, upon rotation, is arranged for translatively moving a second gear member which is prevented from rotating. The clutch mechanism comprises a circumferential shoulder arranged at the second gear member and at least one or a number of resilient clutch fingers with respective inclined inner surfaces arranged at the first gear member, the shoulder arranged for increasingly pressing against the inclined surfaces thereby flexing the clutch fingers outward when the (Continued)

shoulder reaches the clutch fingers in the course of its translation. The clutch mechanism further comprises tube arranged around the clutch fingers, the tube having a number of internal longitudinal splines for engaging the flexed-out clutch fingers.

12 Claims, 7 Drawing Sheets (52) U.S. Cl.
CPC . *A61M 2005/206* (2013.01); *A61M 2005/208* (2013.01); *A61M 2005/3247* (2013.01); *A61M 2205/581* (2013.01)

(56) References Cited

U.S. PATENT DOCUMENTS

| | | | | |
|---|---|---|---|---|
| 5,279,585 A * | 1/1994 | Balkwill | A61M 5/3158 222/309 |
| 5,545,147 A * | 8/1996 | Harris | A61M 5/31551 604/208 |
| 5,643,214 A * | 7/1997 | Marshall | A61M 5/2033 604/131 |
| 5,679,111 A * | 10/1997 | Hjertman | A61M 5/20 604/135 |
| 5,688,251 A * | 11/1997 | Chanoch | A61M 5/3146 222/309 |
| 5,743,889 A * | 4/1998 | Sams | A61M 5/31551 604/207 |
| 5,938,642 A * | 8/1999 | Burroughs | A61M 5/31551 604/208 |
| 6,454,743 B1 * | 9/2002 | Weber | A61M 5/2033 604/131 |
| 7,195,616 B2 * | 3/2007 | Diller | A61M 5/31566 604/207 |
| 7,850,662 B2 * | 12/2010 | Veasey | A61M 5/31546 604/207 |
| 8,317,757 B2 * | 11/2012 | Plumptre | A61M 5/31525 604/211 |
| 2003/0009133 A1 * | 1/2003 | Ramey | A61M 5/1456 604/155 |
| 2005/0203439 A1 * | 9/2005 | Heske | A61B 10/0233 600/566 |
| 2006/0287630 A1 * | 12/2006 | Hommann | A61M 5/2033 604/130 |
| 2012/0083748 A1 * | 4/2012 | Harms | A61M 5/31525 604/224 |
| 2013/0123710 A1 * | 5/2013 | Ekman | A61M 5/2033 604/198 |
| 2013/0274676 A1 * | 10/2013 | Ekman | A61M 5/2033 604/197 |
| 2013/0289490 A1 * | 10/2013 | Kemp | A61M 5/2033 604/198 |
| 2016/0038678 A1 * | 2/2016 | Kemp | A61M 5/2033 604/506 |

OTHER PUBLICATIONS

International Search Report for Int. App. No. PCT/EP2011/052298, completed May 10, 2011.

* cited by examiner

AUTOINJECTOR HAVING PISTON ROD WITH NON-CIRCULAR AXIAL BORE SLIDABLY ARRANGED ON HOUSING SHAFT TO PREVENT RELATIVE ROTATION

CROSS-REFERENCE TO RELATED APPLICATIONS

This application is a U.S. National Phase Application of International Application No. PCT/EP2011/052298 filed Feb. 16, 2011, which claims priority to European Patent Application No. 10153989.8 filed Feb. 18, 2010. The entire disclosure content of these applications are herewith incorporated by references into the present application.

FIELD OF INVENTION

The invention relates to a clutch mechanism for the transmission of rotary movement from a gear arrangement, in particular for use in an auto-injector for releasing a protective needle shroud at the end of an injection stroke.

BACKGROUND

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device.

Administering an injection is a process which presents a number of both mental and physical risks and challenges. The use of an auto-injector can bring many benefits for the user and healthcare professional.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved clutch mechanism for the transmission of rotary movement from a gear arrangement.

The object is achieved by a clutch mechanism according to claim 1.

Preferred embodiments of the invention are given in the dependent claims.

According to the invention a clutch mechanism for transmission of rotary movement from a gear arrangement comprises a first gear member and a second gear member. The first gear member is rotatable about a longitudinal axis but axially fixed. The first gear member, upon rotation, is arranged for translatively moving a second gear member which is prevented from rotating. The clutch mechanism comprises a circumferential shoulder arranged on the second gear member and at least one resilient clutch finger or a number of resilient clutch fingers with respective inclined inner surfaces arranged on the first gear member. The shoulder is arranged for increasingly pressing against the inclined surfaces thereby flexing the clutch fingers outward when the shoulder reaches the clutch fingers in the course of its translation. The clutch mechanism further comprises a tube arranged around the clutch fingers, the tube having a number of internal longitudinal splines for engaging the flexed-out clutch fingers. Prior to being flexed out by the shoulder, the first gear member and its clutch fingers spin without engaging the longitudinal splines of the inner rear tube. When the clutch fingers are flexed out radially they engage with the longitudinal splines in the tube. Thus the rotation of the first gear member is transmitted and forwarded to another component when the second gear member has been advanced to a defined position. The clutch fingers may have respective external teeth protruding radially outwardly in order to provide a defined engagement with the longitudinal splines.

The internal longitudinal splines may be arranged in a manner to form a ratchet when engaged with the clutch fingers. This allows for continued rotation of the first gear member even after the tube has been rotated and hit a stop. By contrast a purely positive locking engagement between the clutch fingers and the longitudinal splines would stall the rotary movement as soon as the tube has hit the stop. Furthermore the ratchet style engagement provides an acoustic feedback for a user.

The clutch mechanism may be applied in an auto-injector for administering a dose of a liquid medicament, the auto-injector further comprising:
  an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing,
  spring means capable of, upon activation, pushing the needle from a covered position inside the housing into an advanced position through the orifice and past the proximal end as well as operating the syringe to supply the dose of medicament,
  activating means arranged to lock the spring means in a pressurized state prior to manual operation and capable of, upon manual operation, releasing the spring means for injection.

In the context of this patent application the term proximal refers to the direction pointing towards the patient during an injection while the term distal refers to the opposite direction pointing away from the patient.

The spring means may be a torsion spring grounded at one end in the housing and at the other end in the first gear member, which is rotatable about a longitudinal axis but axially fixed. The first gear member, upon rotation, is arranged for translatively moving the second gear member. The second gear member is prevented from rotating and coupled to the bung in order to push it towards the proximal end. The first gear member is engaged with the activating means prior to manual operation in a manner to prevent rotation and disengaged from the activating means upon manual operation. The torsion spring is preferably loaded or wound during manufacturing of the auto-injector. When the torsion spring is released by operating the activating means the first gear member starts rotating.

The single torsion spring is used for both, inserting the needle and fully emptying the syringe. A major advantage of the torsion spring is that force is exerted on the bung and syringe in a smooth manner, whereas a conventional compression spring exhibits a rather abrupt force deployment which may spoil a glass syringe or other parts of the auto-injector. The clutch mechanism may be used to transmit rotary motion of the first gear member and forward it to release a needle shroud when the second gear member and the stopper have reached a defined position shortly before the syringe is emptied.

In a preferred embodiment an essentially tube-shaped needle shroud is arranged around the syringe in the housing. The needle shroud is slideable between at least a retracted position with the needle shroud almost hidden inside the housing and an advanced position with the needle shroud protruding from the proximal end and covering the hollow needle in its advanced position. The needle shroud is biased by a second spring means towards the advanced position and locked in the retracted position by a locking means. The locking means is releasable by rotary movement transmitted from the first gear member through the clutch mechanism which is engaged by the second gear member shortly before the second gear member is fully advanced during an injection stroke. Hence, once the dose is complete, the second spring means fires the needle shroud over the needle. This makes the device safer than an equivalent manual injection with respect to needlestick injuries.

In a particularly preferred embodiment an interlock mechanism is arranged for locking the activating means and preventing it from being manually operated. The interlock mechanism may be coupled to the needle shroud. The interlock mechanism may be releasable by pushing the needle shroud a small distance into the housing from the needle shroud's retracted position. Thus, the device cannot be used until the needle shroud is depressed. In normal use this occurs by pushing the device against an injection site, i.e. a patient's skin.

The activating means may be a trigger button laterally arranged at the housing and operable by being pressed transversally with respect to the longitudinal axis. Conventional auto-injectors have the trigger button at their distal end. The advantage of having the trigger button on the side is that the user is less likely to incur an injury should they be confused as to which end the needle will appear from.

The trigger button may have a locking pin engageable with at least one dog tooth provided on the first gear member for preventing rotation thereof in order to lock the spring means or keep it locked in the pressurized state. The dog teeth may be circumferentially arranged at the first gear member thus allowing for stopping the rotation and consequently the injection at any point in time by releasing the trigger button. The trigger button may therefore be biased by a return spring.

The locking means may have the shape of a bayonet fit between the needle shroud and an outer rear tube, which is arranged around the torsion spring. The needle shroud is guided in the housing in a manner to prevent relative rotation, e.g. by at least one spline engaging a respective slot in the housing. The outer rear tube is coupled to the clutch mechanism and may therefore be rotated by the torsion spring. The bayonet fit comprises a bayonet pin and a corresponding pin track arranged between the outer rear tube and the needle shroud. The pin may be held behind a track shoulder in order to hold the needle shroud in its retracted position. In order to release the needle shroud the outer rear tube is rotated by a small angle, thus turning the bayonet pin away from the track shoulder (or vice versa) and into a straight longitudinal part of the pin track. The needle shroud is now released and driven forward from the force of the second spring means, e.g. a compression spring when the auto-injector is removed from the injection site.

The second gear member may be a piston rod having an external lead screw thread. The piston rod may have an axial bore for slidably arranging the piston rod on a shaft attached to the housing. The axial bore and the shaft may have corresponding non-circular profiles in order to prevent relative rotation, e.g. square profiles or profiles with at least one spline or flat. The shaft may be directly or indirectly attached to the housing, e.g. by an end cap. However, the shaft has to be secured against rotation relative to the housing.

The first gear member may be a lead nut engaged with the external lead screw thread. The lead nut may have an internal lead screw thread or a pin guided in the external lead screw thread of the piston rod. Preferably the lead nut is equipped with at least one ball bearing in order to achieve a low friction contact.

In one embodiment the external lead screw thread may have a variable pitch. Thus, speed and force of the needle insertion and injection of the medicament may be adapted to user convenience and to the fact that the torque of the torsion spring is highest when it is fully wound or loaded, and lowest near the end of the injection stroke e.g. the pitch of the thread may be adapted to ensure a quick needle insertion and a relatively slow injection of the medicament in order to cause the least possible pain for the patient.

The interlock mechanism may comprise respective catches provided on the needle shroud and the trigger button. The catches may have the shape of hooks gearing into each other when the needle shroud is in its retracted position. As soon as the needle shroud is pushed in a small distance from the drawn back position the hook shaped catches are laterally shifted out of engagement allowing the trigger button to be operated. In order to allow the needle shroud to be pushed back from the retracted position a small clearance may be provided in the pin track behind the track shoulder.

In a preferred embodiment the syringe is arranged in a syringe carrier and supported by the syringe carrier at a proximal end. Supporting the syringe at its proximal end rather than at its flanges avoids damaging the syringe under load since the flanges are more fragile, in particular in a glass syringe. The syringe carrier is slidably arranged in the needle shroud. An abutment is provided in the needle shroud defining a maximum forward position of the syringe carrier. This allows for defining an injection depth, e.g. for a subcutaneous or intramuscular injection.

The tube of the clutch mechanism is preferably arranged as an inner rear tube arranged around the clutch fingers inside the torsion spring and attached to the outer rear tube at their distal ends.

In a preferred embodiment the internal longitudinal splines are arranged in a manner to form a ratchet when engaged with the clutch fingers. This allows for continued rotation of the lead nut even after the outer rear tube has been rotated and consequently the bayonet pin has hit the side of the longitudinal part of the pin track so the bung may be further forwarded until it bottoms out in the syringe so dead volume is avoided. This is particularly advantageous when using these types of autoinjectors with expensive medicaments. By contrast a purely positive locking engagement between the clutch fingers and the longitudinal splines would stall the rotary movement as soon as the bayonet pin hits the side of the longitudinal part of the pin track leaving residue medicament in the syringe. Furthermore the ratchet style engagement provides an acoustic feedback for the user announcing the upcoming end of the injection. During this time, e.g. ten seconds the user is asked to keep pressure on the injection site.

As the user withdraws the auto-injector from the injection site after the end of injection the needle shroud is pushed over the needle by the compression spring into its advanced position. A locking mechanism may be provided for locking the needle shroud in its advanced position so the needle cannot be re-exposed and needle stick injuries with the now contaminated needle are avoided.

The housing may have at least one viewing window for inspecting the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25]
Exendin-4(1-39)-NH2,
H-(Lys)6-des Pro36, Pro37, Pro38 [Met(O)14, Asp28]
Exendin-4(1-39)-NH2,
H-Asn-(Glu)5-des Pro36, Pro37, Pro38 [Met(O)14, Trp(O2)
25, Asp28] Exendin-4(1-39)-NH2,
des Pro36, Pro37, Pro38 [Met(O)14, Trp(O2)25, Asp28]
Exendin-4(1-39)-(Lys)6-NH2,
H-(Lys)6-des Pro36, Pro37, Pro38 [Met(O)14, Trp(O2)25,
Asp28] Exendin-4(S1-39)-(Lys)6-NH2,
H-Asn-(Glu)5-des Pro36, Pro37, Pro38 [Met(O)14, Trp(O2)
25, Asp28] Exendin-4(1-39)-(Lys)6-NH2;
or a pharmaceutically acceptable salt or solvate of any one
of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitive of the present invention, and wherein.

Corresponding parts are marked with the same reference symbols in all figures.

DETAILED DESCRIPTION

Figure 1:
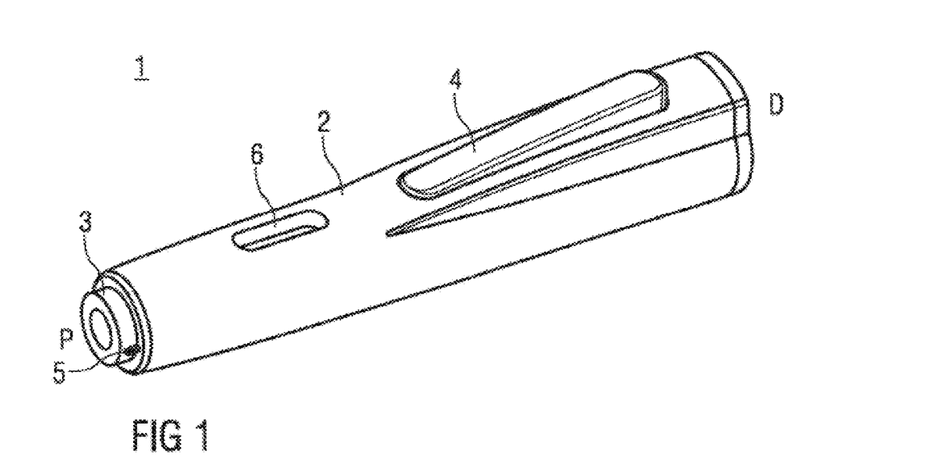
FIG. 1 is a perspective view of an auto-injector with a needle shroud and a lateral trigger button.

FIG. 1 shows a perspective view of an auto-injector 1 with an elongate housing 2 and a needle shroud 3 for protecting a needle (not shown). A lateral trigger button 4 may be transversally pressed in order to trigger an automatic injection. The trigger button 4 is interlocked with the needle shroud 3 so it cannot be pressed until the needle shroud 3 is pushed into the housing 2 by placing it on an injection site, e.g. a patient's skin and applying pressure. The needle shroud 3 has longitudinal splines 5 engaged in corresponding grooves in the housing 1 for preventing relative rotation of the needle shroud 3 with respect to the housing 1. A viewing window 6 allows for viewing and inspecting a syringe held in the auto-injector 1.

Figure 2:
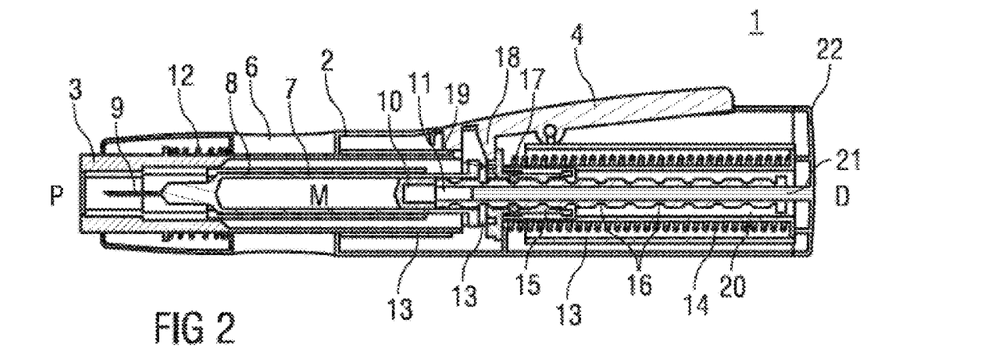
FIG. 2 is a longitudinal section of the auto-injector in a prior to use state.

FIG. 2 shows a longitudinal section of the auto-injector 1 in a prior to use state. A syringe 7 is partially surrounded and supported at a front end by a syringe carrier 8. Attached at the front end of the syringe 7 is a hollow needle 9 for piercing a patient's skin and delivering a liquid medicament M stored inside the syringe 7. Near a back end of the syringe 7 a bung 10 is arranged for sealing the back end. The bung 10 may be advanced by a piston rod 11 in order to expel the medicament M from the syringe 7. The syringe carrier 8 is slidably arranged inside the needle shroud 3. The needle shroud 3 is biased by a compression spring 12 towards a proximal end P. A bayonet fit (shown in FIG. 11) between the needle shroud 3 and an outer rear tube 13 serves for holding the needle shroud 3 in position against the bias of the compression spring 12 prior to use.

A torsion spring 14 is arranged inside the outer rear tube 13 and with one end attached to a distal end D of the housing 2 so torque from the torsion spring 14 is reacted into the housing 2. The other end of the torsion spring 14 is coupled to a lead nut 15 which is rotatably mounted around the piston rod 11. The piston rod 11 has an external lead screw thread 16 engaged with the lead nut 15. The lead nut 15 is equipped with at least one ball bearing 17 for this engagement. It could alternatively have at least one pin. In the prior to use state shown in FIG. 2 the lead nut 15 is biased by the torsion spring 14 but kept from rotating by a locking pin 18 arranged at the trigger button 4 engaged with a dog tooth 19 arranged at the lead nut 15. An inner rear tube 20 is arranged inside the torsion spring 14 and around the piston rod 11 and part of the lead nut 15. The piston rod 11 is guided along a shaft 21 arranged in an axial bore of the piston rod 11. The axial bore and the shaft 21 both have a non-circular profile in order to keep the piston rod 11 from rotating, e.g. a square profile or a profile with at least one spline or flat. The shaft 21 is attached to an end cap 22 arranged at the distal end D of the auto-injector 1.

A protective needle shield (not shown) may be provided which has to be removed prior to use by a user resulting in the situation of FIG. 1. In this situation the needle 9 is a safe distance back within the needle shroud to protect the user from accidental needlestick injuries.

Figure 3:
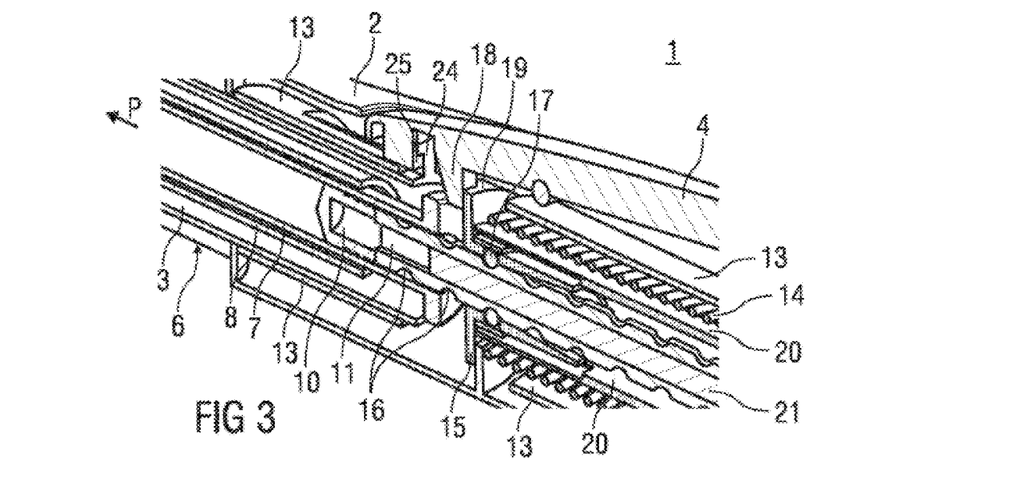
FIG. 3 is a perspective detail view of the longitudinal section of FIG. 2 with the needle shroud and the trigger button interlocked.

FIG. 3 shows a perspective detail view of the longitudinal section of FIG. 2 with the needle shroud 3 and the trigger button 4 interlocked by catches 24, 25 provided at the needle shroud 3 and the trigger button 4, respectively.

Figure 4:
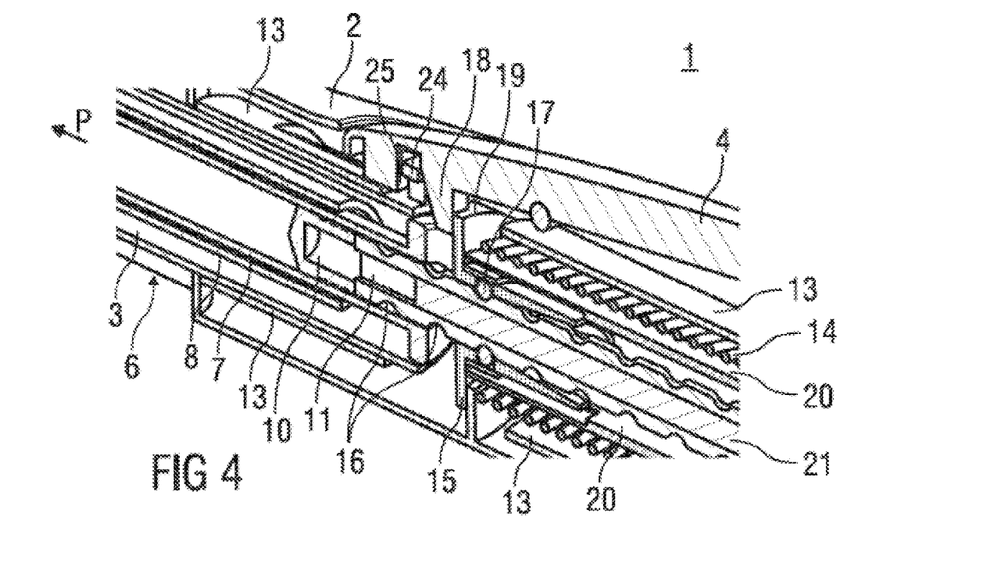
FIG. 4 is a perspective detail view with the trigger button released from the interlock by pressing the needle shroud against an injection site.

In order to prepare for an injection the user pushes the proximal end P of the auto-injector 1 against the injection site. Thus the needle shroud 3 is moved into the auto-injector 1 by a small distance big enough to release the interlocking catches 24, 25 from each other. This situation is shown in FIG. 4. The compression spring 12 opposes the motion of the needle shroud 3 but is specified such that its spring rate and preload are low enough to feel natural for the user. The trigger button 4 may now be operated.

Figure 5:
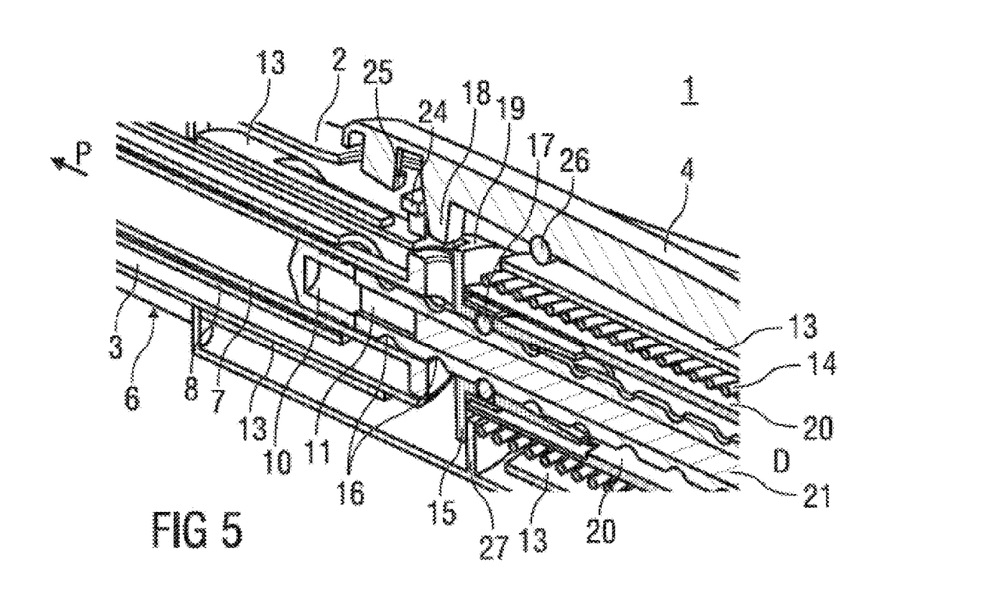
FIG. 5 is a perspective detail view with the trigger button pressed.

FIG. 5 shows the distal end of the trigger button 4 being pressed thus rotating the trigger button 4 about a trigger pivot 26 in the housing 2, raising the proximal end of the trigger button 4 and moving the locking pin 18 out of the engagement with the dog tooth 19 of the lead nut 15. Thus the lead nut 15 is released and torque from the torsion spring 14 causes the lead nut 15 to rotate. Since the lead nut 15 abuts against a thrust face 27 in the housing 2 it is kept from moving in distal direction D due to the load applied to the piston rod 11 while rotating.

Figure 6:
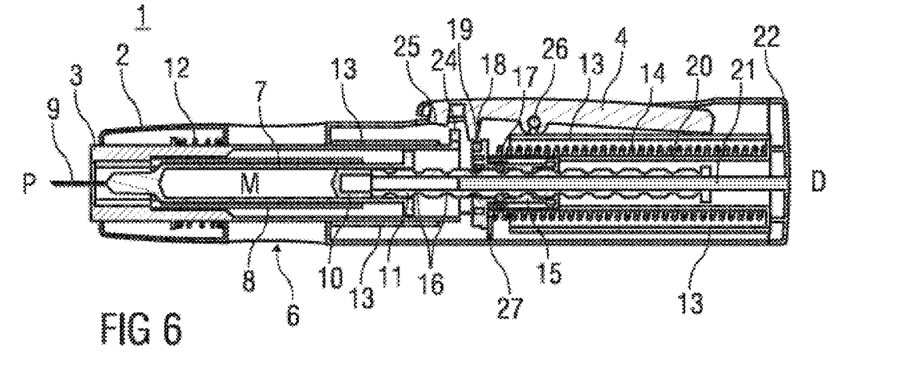
FIG. 6 is a longitudinal section of the auto-injector with a syringe and an injection needle advanced in order to pierce a patient's skin.

Instead, as shown in FIG. 6, the piston rod 11, kept from rotating by the shaft 21, is pushed forward in proximal direction P due to the engagement of the lead nut 15 and the lead screw thread 16. The advancing piston rod 11 pushes against the bung 10 which in turn advances the syringe 7 by virtue of the friction between the bung 10 and the syringe wall and due to the thin fluid channel inside the hollow needle 9 opposing the displacement of the medicament M. The advancing syringe 7 also causes the needle 9 to protrude beyond the proximal end P of the auto-injector 1 into the injection site, e.g. the patient's skin. Since the syringe 7 is supported at its proximal end by an orifice of the syringe carrier 8 the syringe carrier 8 is also advanced with the syringe 7 until the syringe carrier 8 abuts against an abutment in the needle shroud 3. This contact sets the injection depth relative to the needle shroud 3.

Figure 7:
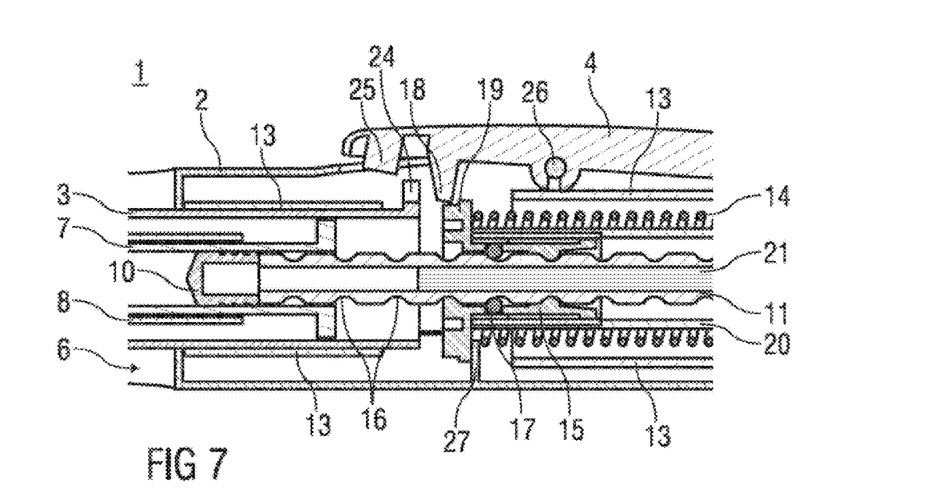
FIG. 7 is a detail view of the longitudinal section of FIG. 6.

FIG. 7 is a detail view of the longitudinal section of FIG. 6.

After the syringe carrier 8 has hit the abutment of the needle shroud 3 the syringe 7 is kept from advancing further.

With the lead nut 15 still rotating and pushing the piston rod 11 the bung 10 overcomes the friction and the hydraulic resistance of the medicament M and advances inside the syringe 7 thereby displacing the medicament M and delivering it through the fluid channel of the hollow needle 9 into or through the patient's skin. This situation is shown in FIG. 8.

Figure 8:
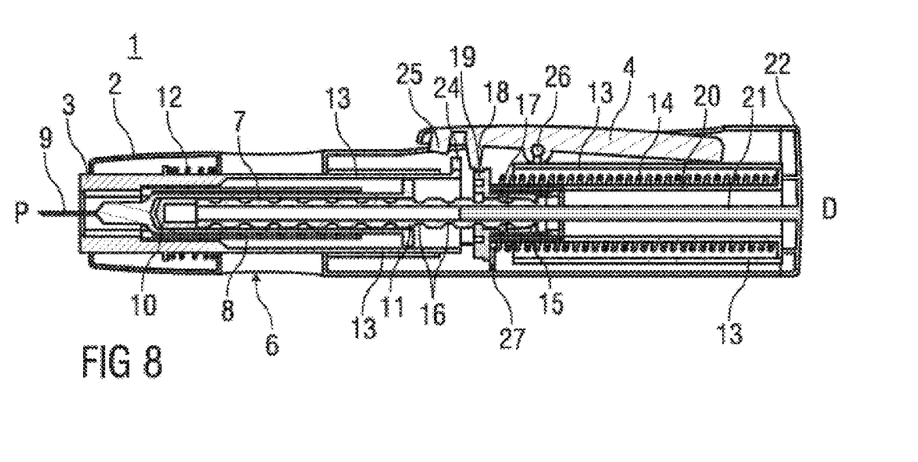
FIG. 8 is a longitudinal section of the auto-injector with a piston rod advancing a bung in order to expel a liquid medicament from the syringe.
Figure 9:
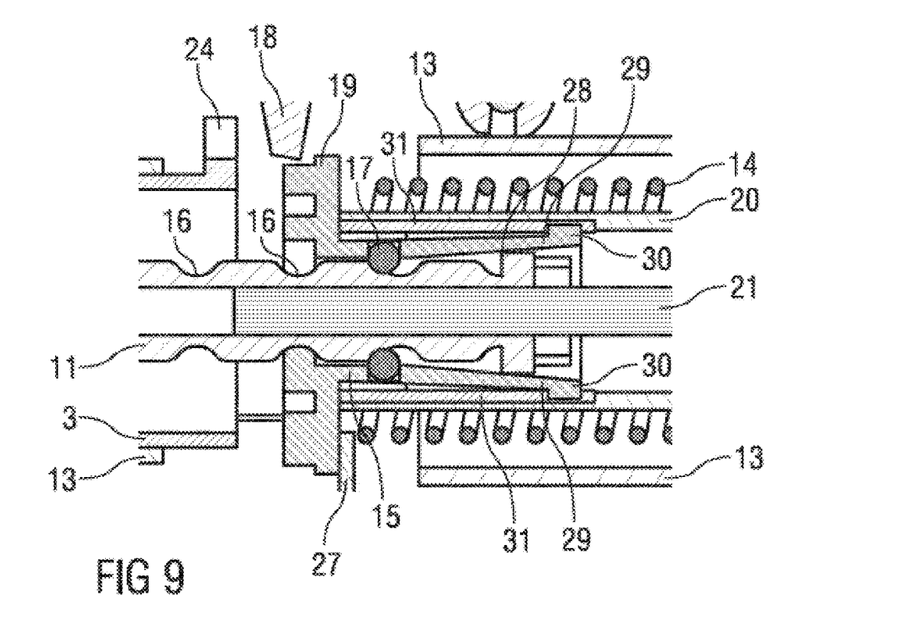
FIG. 9 is a detail view of FIG. 8 with a clutch mechanism.
Figure 10A:
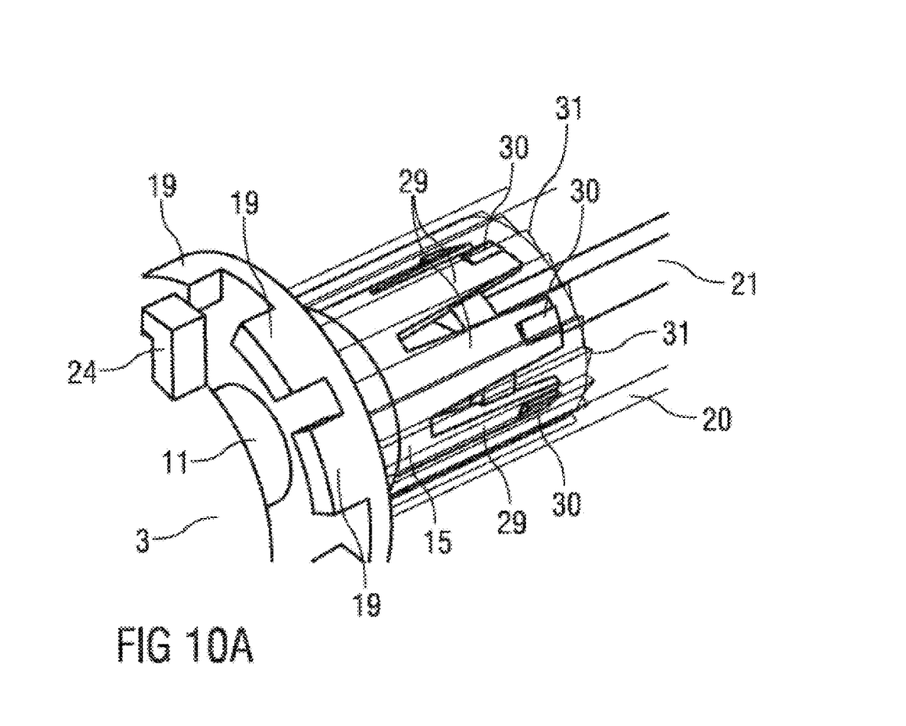
FIG. 10 shows perspective views of two alternative clutch mechanisms.
Figure 10B:
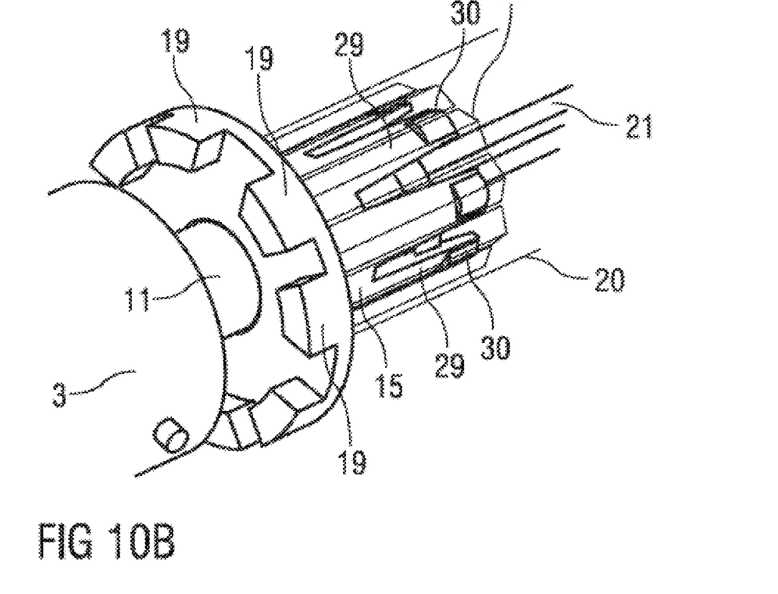

FIG. 8 shows the piston rod 11 and the bung 10 almost fully advanced and the syringe 7 almost entirely emptied but for a small residue. Referring now to FIGS. 9 and 10a and b showing different detail views of the cut-out marked in FIG. 8, just before the bung 10 bottoms out in the syringe 7 a shoulder 28 on the distal end of the piston rod 11 behind the lead screw thread 15 is pushed into clutch fingers 29 on the distal end of the lead nut 15 thereby bending the clutch fingers 29 radially outward. Each clutch finger 29 has an external tooth 30 which now engages with a respective internal longitudinal spline 31 provided in the proximal end of the inner rear tube 20, causing the inner rear tube 20 to rotate along with the lead nut 15. The splines 31 are arranged in a ratchet manner in FIG. 10a. FIG. 10b shows an alternative embodiment with rounded finger teeth 30. In both embodiments (FIGS. 10a and 10b) the clutch mechanism is arranged to let the clutch fingers 29 generate enough torque on the longitudinal splines 31 to partially rotate the outer rear tube 13 to release a bayonet fit described below in FIG. 11. However the torque generated has to be low enough to let the lead nut 15 continue rotating with the spring arms jumping over the splines 31 and making a rattling noise indicating that the injection has been nearly finished. The inner rear tube 20 is coupled with the outer rear tube 13 near the distal end D of the auto-injector 1 (cf. FIG. 8). Thus the outer rear tube 13 is also rotated. The outer tube 13 has a circumferential slot (not illustrated) to allow the distal end of the torsion spring to pass through to the housing 2 for grounding the torsion spring 14. The circumferential slot has to be long enough to allow a partial rotation of the outer rear tube 13 in order to disengage the bayonet fit described below in FIG. 11.

Figure 11:
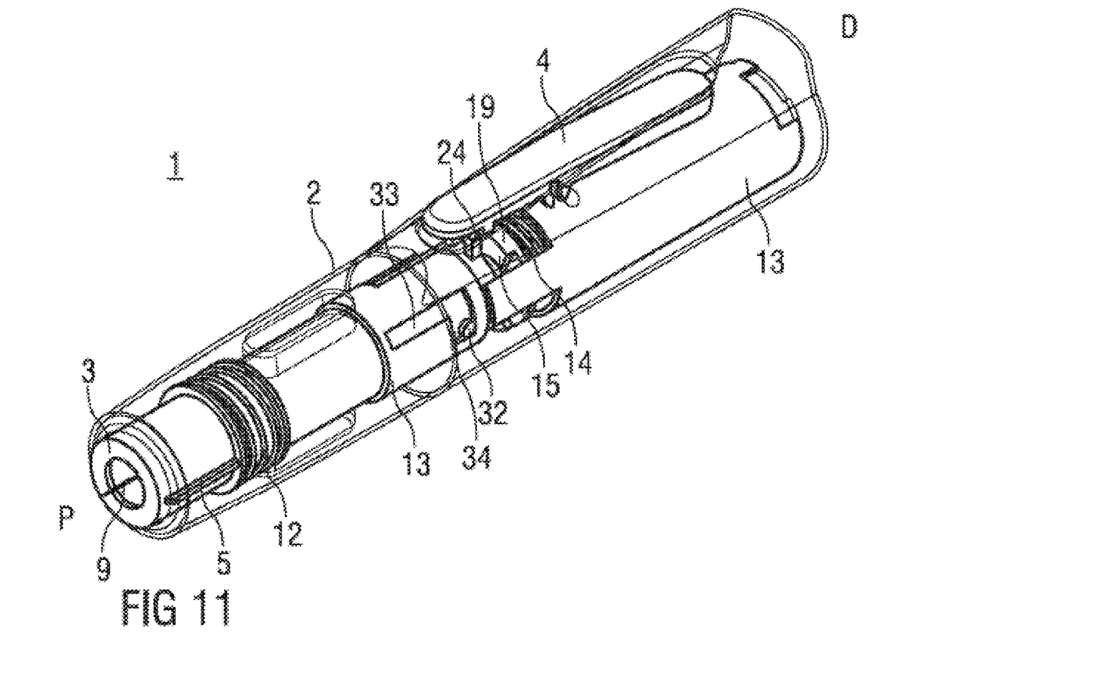
FIG. 11 is a perspective view of the auto-injector with a bayonet fit between the needle shroud and an outer rear tube, the needle shroud prevented from moving forward.

FIG. 11 shows a perspective view of the auto-injector 1 just before the engagement of the clutch fingers 29 with the internal longitudinal splines 31. The bayonet fit between a pin 32 of the needle shroud 3 and a pin track 33 of the outer rear tube 13 is still in a state with the pin 32 behind a track shoulder 34 so the needle shroud 3 would be held in position against the bias of the compression spring 12 if the still depressed needle shroud 3 was released. A small axial clearance behind the track shoulder 34 allows the needle shroud 3 to be pushed in distal direction D just enough to disengage the interlock between the button 4 and the needle shroud 3 as described above.

Figure 12:
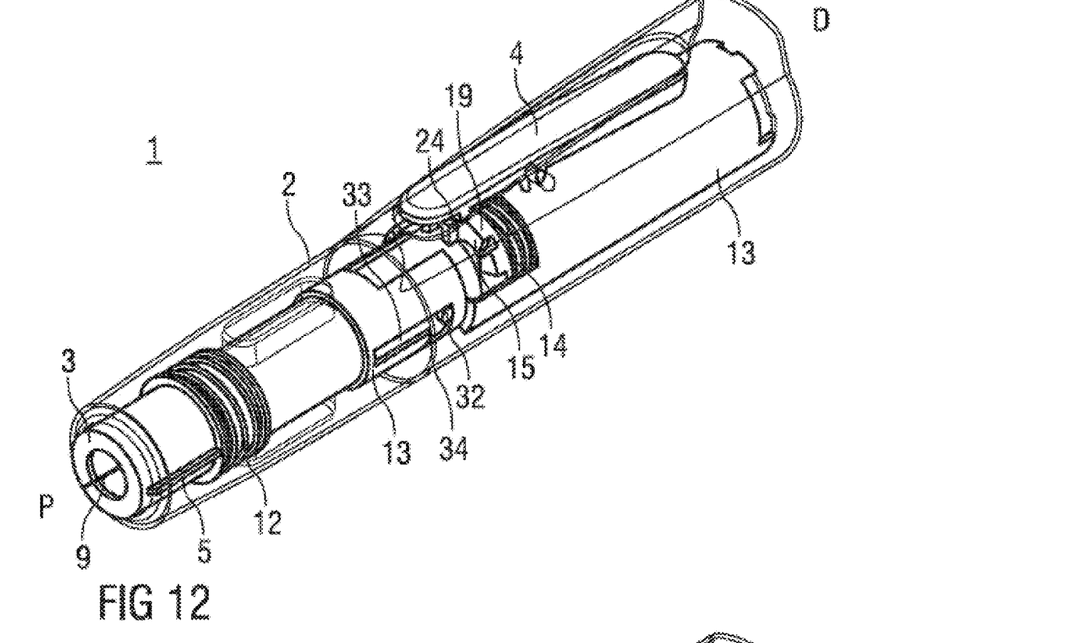
FIG. 12 is a perspective view of the auto-injector with the bayonet fit, the outer rear tube rotated in order to allow the needle shroud to move forward.

When the clutch fingers 29 are engaged with the internal longitudinal splines 31 the outer rear tube 13 is rotated so as to disengage the bayonet fit by the pin 32 coming clear of the track shoulder 34 so the needle shroud 3 may be pushed forward by the compression spring 12 (see FIG. 12). At this point the user is asked to keep pressure with the auto-injector 1 at the injection site for a short period of time, e.g. ten seconds. During this time the lead nut 15 is still rotating and forwarding the piston rod 11 and bung 10 until the bung 10 bottoms out at the proximal end of the syringe 7 thereby virtually entirely displacing the rest of the medicament M from the syringe 7.

Figure 13:
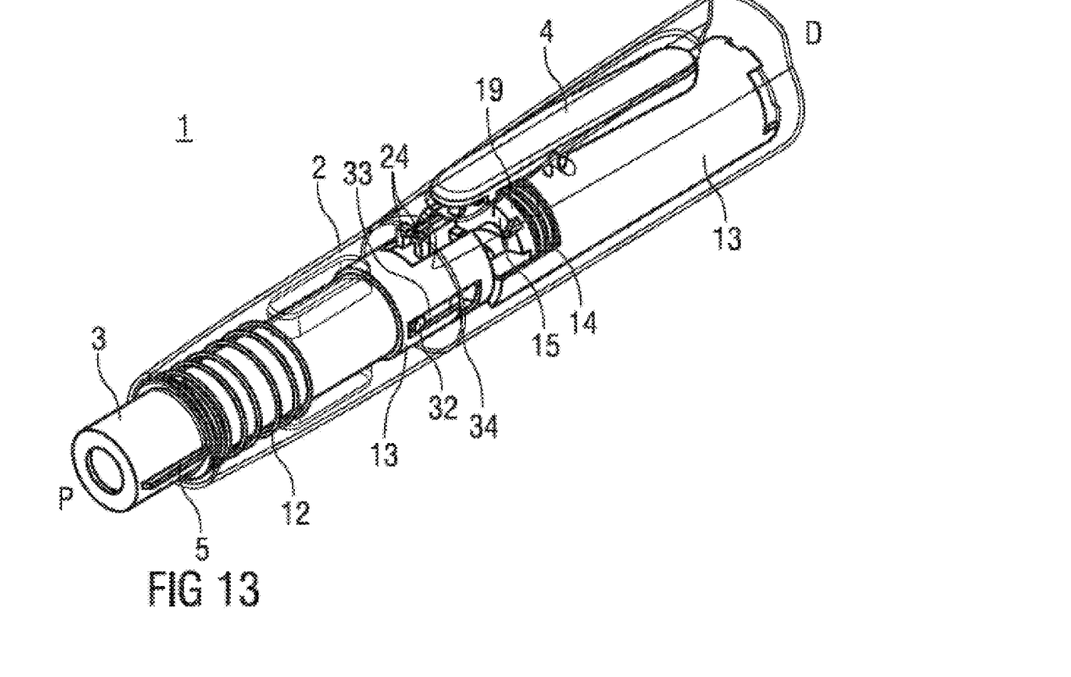
FIG. 13 is a perspective view of the auto-injector with the bayonet fit, the needle shroud pushed forward by means of a bias spring.
Figure 14:
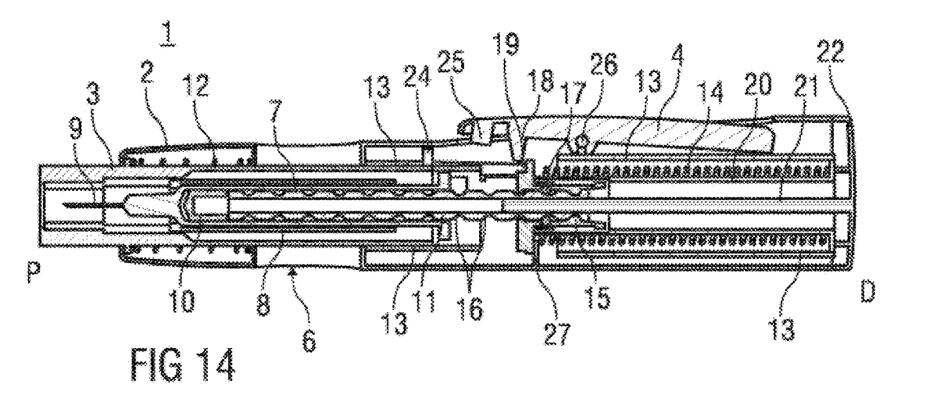
FIG. 14 is a longitudinal section of the auto-injector with the needle shroud fully advanced and locked in forward position in order to protect the needle.

As the user withdraws the auto-injector 1 from the injection site the needle shroud 3 is pushed over the needle 9 in proximal direction P by the compression spring 12. This situation is shown in FIGS. 13 and 14. A locking mechanism may be provided to lock the needle shroud 3 in this extended needle protection position in order to prevent further exposure of the needle. The locking mechanism may be a unidirectional barb or a similar means known to those skilled in the art.

The invention claimed is:

1. An auto-injector for administering a dose of a liquid medicament comprising:
   a clutch mechanisms;
   an elongate housing arranged to contain a syringe with a hollow needle and a bung for sealing the syringe and displacing the medicament, the elongate housing having a distal end and a proximal end with an orifice intended to be applied against an injection site, wherein the syringe is slidably arranged with respect to the housing,
   a torsion spring capable of, upon activation, pushing the needle from a covered position inside the housing into an advanced position through the orifice and past the proximal end as well as operating the syringe to supply the dose of medicament, the torsion spring arranged around a tube,
   a button arranged to lock the torsion spring in a pressurized state prior to manual operation and capable of, upon manual operation, releasing the torsion spring for injection,
   wherein the torsion spring is grounded at one end in the housing and at the other end in a first gear member, wherein a piston rod is coupled to the bung in order to push it towards the proximal end, the piston rod having an axial bore for slidably arranging the piston rod on a shaft attached to the housing, the axial bore and the shaft having corresponding non-circular profiles, wherein the first gear member is engaged with the button prior to manual operation in a manner to prevent rotation and wherein the first gear member is disengaged from the button upon manual operation, wherein a tube-shaped needle shroud is arranged around the syringe in the housing, the needle shroud slideable between at least a drawn back position with a portion of the needle shroud hidden inside the housing and an advanced position with more than the portion of the needle shroud protruding from the proximal end and covering the hollow needle in its advanced position, wherein the needle shroud is biased by a second spring towards the advanced position and locked in the drawn back position by a lock which is releasable by rotary movement transmitted by the clutch mechanism which is engaged by the piston rod before the piston rod is fully advanced during an injection stroke.

2. The auto-injector of claim 1, wherein the clutch mechanism for transmission of the rotary movement from a gear arrangement comprises a first gear member and the piston rod, the first gear member rotatable about a longitudinal axis but axially fixed wherein the first gear member, upon rotation, is arranged for translatively moving the piston rod which is prevented from rotating, wherein the clutch mechanism comprises a circumferential shoulder arranged at the piston rod and at least one resilient clutch finger with a respective inclined inner surface arranged at the first gear member, the shoulder arranged for increasingly pressing against the inclined surface thereby flexing the at least one clutch finger outward when the shoulder reaches the at least one clutch finger in the course of its translation, wherein the clutch mechanism further comprises the tube arranged around the at least one clutch finger, wherein the at least one clutch finger is flexed forming a flexed-out clutch finger, the tube having a number of internal longitudinal splines for engaging the flexed-out clutch finger.

3. The auto-injector mechanism according to claim 2, wherein the piston rod has an external lead screw thread, wherein the first gear member is a lead nut engaged with the external lead screw thread.

4. The auto-injector mechanism according to claim 3, wherein the lead nut is provided with an internal lead screw thread or with at least one pin or with at least one ball bearing for engaging the external lead screw thread.

5. The auto-injector mechanism according to claim 3, wherein the external lead screw thread has a variable pitch.

6. The auto-injector mechanism according to claim 2, wherein the number of internal longitudinal splines are arranged in a manner to form a ratchet when engaged with the at least one clutch finger.

7. The auto-injector mechanism according to claim 2, wherein the clutch mechanism comprises a plurality of resilient clutch fingers including the at least one clutch finger, wherein each clutch finger of the plurality of resilient clutch fingers has a respective external tooth arranged for engaging the number of internal longitudinal splines.

8. The auto-injector according to claim 1, wherein a locking mechanism is provided for locking the needle shroud in its advanced position.

9. The auto-injector according to claim 1, wherein an interlock mechanism is arranged for locking the button and preventing it from being manually operated, wherein the interlock mechanism is coupled to the needle shroud, wherein the interlock mechanism is releasable by pushing the needle shroud a distance into the housing from the needle shroud's retracted position.

10. The auto-injector according to claim 1, wherein the syringe is arranged in a syringe carrier and supported by the syringe carrier at a proximal end of the syringe, wherein the syringe carrier is slidably arranged in the needle shroud and wherein an abutment is provided in the needle shroud defining a maximum forward position of the syringe carrier.

11. The auto-injector according to claim 1, wherein at least one viewing window for inspecting the syringe is provided in the housing.

12. The auto-injector according to claim 1, wherein the syringe carries a medicament consisting of at least one pharmaceutically active compound.

* * * * *